United States Patent [19]

Cramer

[11] 4,161,609

[45] Jul. 17, 1979

[54] SYNTHESIS OF CARBOXYLIC ACID ESTERS

[75] Inventor: Richard D. Cramer, Landenberg, Pa.

[73] Assignee: E. I. Du Pont de Nemours and Company, Wilmington, Del.

[21] Appl. No.: 833,371

[22] Filed: Sep. 14, 1977

[51] Int. Cl.$^2$ .............................................. C07C 67/20
[52] U.S. Cl. ........................................ 560/215; 560/8; 560/129; 560/130; 560/205; 560/231
[58] Field of Search ................... 560/8, 129, 130, 205, 560/215, 231

[56] References Cited

U.S. PATENT DOCUMENTS

| 3,442,934 | 5/1969 | Pine | 560/205 |
|---|---|---|---|
| 3,639,461 | 2/1972 | Ito et al. | 560/205 |

OTHER PUBLICATIONS

Arifdzhanov, A. et al. "Esterification of Formic Acid by Ethyl Alcohol in the Presence of Aluminosilicate." Tr. Tashk. Politekh. Inst. (1972) 90, 44–45. Cited in Chemical Abstracts, vol. 83 (1975) Item No. 96, 371j.
Kirk–Othmer "Encyclopedia of Chemical Technology" Interscience Publ. 2nd Ed. 1964, vol. 2 at p. 69. Ibid. vol. 8 at pp. 339–340.
Urdong, et al. College Dictionary, 1969, Random House Publ. at p. 1060.
Fieser, Louis F. et al. Organic Chemistry, 1944, D. C. Heath Publ. at p. 123.
Hackh's Chemical Dictionary, 1975, McGraw-Hill Publ. at p. 431.

*Primary Examiner*—Bernard Helfin
*Assistant Examiner*—L. Hendriksen

[57] ABSTRACT

A method is provided for converting a carboxylic acid amide to a carboxylic acid ester by reacting a vaporized mixture of the amide and an aliphatic alcohol or a phenol in the presence of a suitable catalyst at temperatures of from 100° C. to 400° C. The process is especially useful for the conversion of methacrylamide to methyl methacrylate.

26 Claims, No Drawings

SYNTHESIS OF CARBOXYLIC ACID ESTERS

BACKGROUND OF THE INVENTION

1. Field of the Invention

This invention concerns a process for converting carboxylic acid amides to the corresponding carboxylic acid esters by reacting a vaporized mixture of the amides and lower aliphatic alcohols in the presence of a suitable catalyst. More particularly, the process is directed to the conversion of methacrylamide to methyl methacrylate.

2. Relation to the Prior Art

1. U.S. Pat. No. 2,913,486 claims a one-step process of reacting an unsaturated aliphatic nitrile, specifically acrylonitrile or methacrylonitrile, with a lower aliphatic alcohol and a molar amount of water in the vapor phase over a solid esterification catalyst at 400°–800° F. (204°–427° C.), preferably at 600°–650° F. (315°–344° C.) to produce methyl acrylate or methyl methacrylate. The solid esterification catalysts disclosed are silica, silica-alumina, titania, thoria, and zirconia. The catalyst activity may be enhanced by small amounts of phosphoric or molybdic acid, and the catalyst may include promoters such as platinum, nickel, iron, copper and silver. The preferred catalyst is silica.

2. U.S. Pat. No. 3,466,320 claims a one-step process of preparing a lower alkyl ester of an $\alpha,\beta$-unsaturated acid from the corresponding $\alpha,\beta$-unsaturated nitrile, water, and a lower alkanol in the vapor phase in the presence of a solid esterification catalyst containing 1% of niobium pentoxide at temperatures of 150°–500° C. Preferred catalysts are silica, alumina, titanium dioxide, zirconia, and mixtures thereof, and preferred reactants are acrylonitrile, methacrylonitrile, methanol and ethanol.

3. Japanese Patent Publication (Kokai) 72-25, 120 discloses a vapor-phase process for converting acrylonitrile, methanol and water to methyl acrylate in the presence of solid catalysts at 250° C. Mixtures of boric oxide with alumina, titania, silica, zinc oxide and zirconia are disclosed as suitable catalysts.

4. The references listed herein below relate to the conversion of carboxylic acid amides and nitriles to esters by liquid phase processes in mineral acid media such as sulfuric and phosphoric acids. Unsaturated nitriles such as methacrylonitrile may be generated in situ from ketone cyanohydrins such as acetone cyanohydrin. In the presence of stoichiometric amounts of added water, these nitriles are converted to the corresponding amides which may be isolated before they are reacted with alcohols to form ester products. During such reactions, the mineral acid is consumed stoichiometrically and converted to the ammonium salt of the acid by the ammonia liberated.

Such processes are disclosed in:

(a) A. Bonz. *Zeitschr. physik. Chem.*, (A), 2, 865–900 (1888);

(b) L. Meyer, *Ber.*, 22, 24 (1889);

(c) U.S. Pat. Nos. 3,332,984 and 3,406,120.

5. Other processes in solution which have been used to convert amides to esters are disclosed in the following references:

(a) Belgian Pat. No. 843,436 (West German equivalent, Auslegeschrift No. 2528524) claims a process of preparation of carboxylic esters from the corresponding amides using a metal carboxylate catalyst;

(b) French Pat. No. 1,161,140 (West German equivalent, Auslegeschrift, No. 1,071,689) claims a process of making aromatic carboxylic esters from the corresponding amides using an alkaline catalyst;

(c) E. H. White, *J. Amer. Chem. Soc.*, 76, 4497 (1954) and 77, 6011 (1955) describes the conversion of a secondary amide to an ester by N-nitrosation and thermal decomposition according to the reaction:

(d) J. S. Matthews and J. P. Cookson, *J. Org. Chem.*, 34, 3204 (1969) describe the reaction of amides with alkyl halides in aqueous media to produce esters according to the reaction:

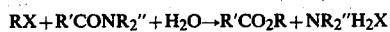

(e) D. H. R. Barton, A. L. J. Beckwith and A. Goosen, *J. Chem. Soc.*, 181 (1965) describe the photolysis of N-iodoamides to lactones (internal esters):

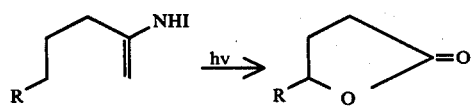

None of the above-listed references discloses a process for converting carboxylic acid amides to carboxylic acid esters by reacting the amides and lower aliphatic alcohols in the vapor phase in the presence of the catalysts disclosed hereinbelow at 100° C. to 400° C.

SUMMARY OF THE INVENTION

This invention is a process for the preparation of carboxylic acid esters from the corresponding carboxylic acid amides and aliphatic alcohols and phenols according to the following equation:

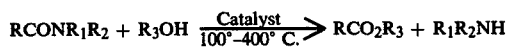

in which:

R is H; alkyl of from 1 to 10 carbon atoms; alkenyl of from 2 to 10 carbon atoms; alkynyl of from 2 to 10 carbon atoms; phenyl; or phenyl substituted by a methyl, chloro or methoxy group;

$R_1$ and $R_2$, taken separately, are individually H or alkyl groups of from 1 to 10 carbon atoms;

$R_1$ and $R_2$, taken together, may be $(CH_2)_4$ or $(CH_2)_5$;

$R_3$ is a primary or secondary alkyl group of from 1 to 10 carbon atoms; a primary or secondary alkyl group of from 2 to 10 carbon atoms substituted by a hydroxy group, alkoxy group of from 1 to 4 carbon atoms or acetoxy group; phenyl; or phenyl substituted by one or two alkyl groups of from 1 to 10 carbon atoms, one or two fluorine, chlorine or bromine atoms, a methoxy or a methoxycarbonyl group.

The catalyst is titanium dioxide ($TiO_2$), alumina ($Al_2O_3$), zirconium dioxide ($ZrO_2$), molybdena ($MoO_3$), cerium (IV) oxide ($CeO_2$), mixtures of silica ($SiO_2$) and alumina inclusive of compositions comprising from 10 to 100% alumina and from 90 to 0% silica, mixtures of titanium dioxide and alumina inclusive of compositions comprising 0 to 100% titanium dioxide and 100 to 0% alumina, or supported catalysts inclusive of compositions comprising from 5 to 25% vanadium pentoxide ($V_2O_5$), nickel oxide (NiO) or tungsten (VI) oxide ($WO_3$) on alumina, or alumina-silica mixtures as defined above, or mixtures of copper (II) oxide (CuO) and chromium (III) oxide ($Cr_2O_3$). The reaction is carried out continuously or semi-continuously in the vapor phase at temperatures of from 100° to 400° C. and pressures of from 0.01 to 100 atmospheres, and in which there is at least a 1:1 molar ratio of alcohol or phenol to amide in the reactant feed.

In a preferred embodiment of the process of this invention: R is H; alkyl of from 1 to 4 carbon atoms; alkenyl of from 2 to 4 carbon atoms; alkynyl of from 2 to 4 carbon atoms; phenyl; or phenyl substituted by a methyl, chloro or methoxy group; $R_1$ and $R_2$, taken separately, are individually H or alkyl groups of from 1 to 4 carbon atoms; and $R_3$ is a primary or secondary alkyl of from 1 to 6 carbon atoms; a primary or secondary alkyl of from 2 to 4 carbon atoms substituted by a hydroxy group; alkoxy group of from 1 to 4 carbon atoms or an acetoxy group; phenyl; or phenyl substituted by one or two alkyl groups of from 1 to 4 carbon atoms, one or two fluorine, chlorine or bromine atoms, a methoxy or a methoxycarbonyl group.

An especially preferred process is the conversion of methacrylamide

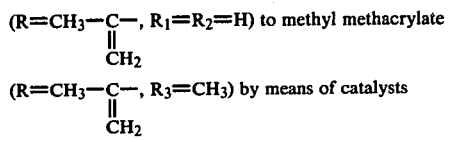

comprising an alumina-silica combination whose composition is about 90% alumina and 10% silica, or zirconium dioxide, at temperatures in the range of 200°-275° C., preferably about 250° C., at pressures of from 0.2 to 5 atmospheres, preferably 1 atmosphere, at a methacrylamide:methanol feed ratio in the range of 1:4 to 1:20, preferably in the range of 1:4 to 1:8.

DETAILED DESCRIPTION OF THE INVENTION

Unless otherwise stated all parts and percentages used herein are by weight and all temperatures are in degrees Centigrade.

The carboxylic acid amides useful as starting materials for the process of this invention must be sufficiently volatile at the reaction temperatures of 100°-400° C. in order to be contacted in the vapor phase with the alcohol or phenol chosen. The reaction proceeds satisfactorily with equimolar or excess amounts of the alcohol or phenol component, introduced either as a mixture with the amide component or individually. An inert solvent, especially an aliphatic or alicyclic ether (e.g. 1,4-dioxan, 1,2-dimethoxyethane (glyme), 1-methoxy-2-(2-methoxyethoxy)ethane (diglyme) or tetrahydrofuran) may be incorporated into one or more of the feed materials to promote solubility of the reactants for ease of introduction. However, the presence of a large amount of unreacted or nonreactive diluent makes the process uneconomical because of the size of the investment required in reagents, in energy to vaporize the reagents, and in means to separate the reagents from the ester product.

Suitable amides include, inter alia, the primary, secondary and tertiary amides listed in Table I.

Table I

| Name | Carboxylic Acid Amides Structure | bp | mp |
|---|---|---|---|
| Primary Amides | | | |
| Formamide | $HCONH_2$ | 111° C. (20 mm) | |
| Acetamide | $CH_3CONH_2$ | 222° C. | |
| Propanamide | $CH_3CH_2CONH_2$ | 213° C. | |
| Butanamide | $CH_3CH_2CH_2CONH_2$ | 216° C. | |
| 2-Methylpropanamide | $(CH_3)_2CHCONH_2$ | | 128° C. |
| Pentanamide | $CH_3(CH_2)_3CONH_2$ | | 106° C. |
| 3-Methylbutanamide | $(CH_3)_2CHCH_2CONH_2$ | 224° C. | |
| 2,2-Dimethylpropanamide | $(CH_3)_3CCONH_2$ | 212° C. | |
| 2-Propenamide (Acrylamide) | $CH_2{=}CHCONH_2$ | | 85° C. |
| cis-2-Butenamide (cis-Crotonamide) | $\begin{array}{c}CH_3\phantom{xx}CONH_2\\ \diagdown\phantom{x}\diagup\\ C{=}C\\ \diagup\phantom{x}\diagdown\\ H\phantom{xxxx}H\end{array}$ | | 102° C. |
| trans-2-Butenamide (trans-Crotonamide) | $\begin{array}{c}CH_3\phantom{xxx}H\\ \diagdown\phantom{x}\diagup\\ C{=}C\\ \diagup\phantom{x}\diagdown\\ H\phantom{xx}CONH_2\end{array}$ | | 158° C. |
| 2-Methyl-2-propenamide (Methacrylamide) | $\underset{\underset{CH_2}{\|\|}}{CH_3CCONH_2}$ | | 102° C. |
| trans-2-Pentenamide | $\begin{array}{c}C_2H_5\phantom{xx}H\\ \diagdown\phantom{x}\diagup\\ C{=}C\\ \diagup\phantom{x}\diagdown\\ H\phantom{xx}CONH_2\end{array}$ | | 148° C. |
| cis-2-Methyl-2-butenamide | $\begin{array}{c}CH_3\phantom{xx}CH_3\\ \diagdown\phantom{x}\diagup\\ C{=}C\\ \diagup\phantom{x}\diagdown\\ H\phantom{xx}CONH_2\end{array}$ | | 75° C. |
| 2-Ethyl-2-propenamide (Ethacrylamide) | $\underset{\underset{CH_2}{\|\|}}{CH_3CH_2CCONH_2}$ | | 83.5° C. |

Table I-continued

Carboxylic Acid Amides

| Name | Structure | bp | mp |
|---|---|---|---|
| 3-Methyl-2-butenamide (3,3-Dimethylacrylamide) | $(CH_3)_2C=CHCONH_2$ | | 107° C. |
| Propynamide | $CH\equiv CCONH_2$ | | 61° C. |
| 2-Butynamide | $CH_3C\equiv CCONH_2$ | | 147° C. |
| 2-Pentynamide | $CH_3CH_2C\equiv CCONH_2$ | | |
| Benzamide | $C_6H_5CONH_2$ | 288° C. | |
| 2-Methylbenzamide (2-Toluamide) | $2\text{-}CH_3C_6H_4CONH_2$ | | 147° C. |
| 3-Methylbenzamide (3-Toluamide) | $3\text{-}CH_3C_6H_4CONH_2$ | | 97° C. |
| 4-Methylbenzamide (4-Toluamide) | $4\text{-}CH_3C_6H_4CONH_2$ | | 155° C. |
| 2-Chlorobenzamide | $2\text{-}ClC_6H_4CONH_2$ | | 142° C. |
| 3-Chlorobenzamide | $3\text{-}ClC_6H_4CONH_2$ | | 134° C. |
| 4-Chlorobenzamide | $4\text{-}ClC_6H_4CONH_2$ | | 179° C. |
| 2-Methoxybenzamide | $2\text{-}CH_3OC_6H_4CONH_2$ | | 129° C. |
| 4-Methoxybenzamide | $4\text{-}CH_3OC_6H_4CONH_2$ | 295° C. | |
| Secondary Amides | | | |
| N-Methylacetamide | $CH_3CONHCH_3$ | 141° C. (90 mm) | |
| N-Methylpropanamide | $CH_3CH_2CONHCH_3$ | 146° C. (90 mm) | |
| N-Methylbutanamide | $CH_3CH_2CH_2CONHCH_3$ | 156° C. (90 mm) | |
| N-Methylbenzamide | $C_6H_5CONHCH_3$ | 291° C. | |
| N-Ethylacetamide | $CH_3CONHC_2H_5$ | 205° C. | |
| N-(1-Propyl)acetamide | $CH_3CONHCH_2CH_2CH_3$ | 222° C. | |
| N-(1-Butyl)acetamide | $CH_3CONH(CH_2)_3CH_3$ | 229° C. | |
| Tertiary Amides | | | |
| N,N-Dimethylformamide | $HCON(CH_3)_2$ | 152° C. | |
| N,N-Dimethylacetamide | $CH_3CON(CH_3)_2$ | 165° C. | |
| N,N-Dimethylpropanamide | $CH_3CH_2CON(CH_3)_2$ | 176° C. | |
| N,N-Dimethylbutanamide | $CH_3(CH_2)_2CON(CH_3)_2$ | 125° C. (100 mm) | |
| N,N-Diethylacetamide | $CH_3CON(C_2H_5)_2$ | 186° C. | |
| N,N-Diethylpropanamide | $CH_3CH_2CON(C_2H_5)_2$ | 191° C. | |
| N-Methyl-N-ethyl-acetamide | $CH_3CON(CH_3)C_2H_5$ | 180° C. | |
| N,N-Di(1-propyl)acetamide | $CH_3CON(CH_2CH_2CH_3)_2$ | 209° C. | |
| N,N-Di(1-butyl)acetamide | $CH_3CON((CH_2)_3CH_3)_2$ | | |
| N-Acetylpiperidine | $CH_3CON\text{-piperidinyl}$ | 226° C. | |
| N-Benzoylpyrrolidine | $C_6H_5CON\text{-pyrrolidinyl}$ | 190° C. (12 mm) | |

The alcohols and phenols useful as starting materials for the process of this invention must be sufficiently volatile at the reaction temperature of 100°–400° C. in order to be contacted in the vapor phase with the carboxylic acid amide chosen.

Alcohols which are suitable starting materials include primary and secondary alcohols. Tertiary alcohols are dehydrated to ethers and olefins under the reaction conditions, and are therefore generally not useful in this synthesis. A wide variety of phenols with one or two substituents on the aromatic ring are suitable starting materials. Useful alcohols and phenols are listed in Table II.

Table II

Alcohols and Phenols

| Name | Structure | bp |
|---|---|---|
| Alcohols | | |
| Methanol | $CH_3OH$ | 65° C. |
| Ethanol | $CH_3CH_2OH$ | 78.5° C. |
| 1-Propanol | $CH_3CH_2CH_2OH$ | 97° C. |
| 2-Propanol | $(CH_3)_2CHOH$ | 82° C. |
| 1-Butanol | $CH_3(CH_2)_3OH$ | 118° C. |
| 2-Butanol | $CH_3CH_2CH(CH_3)OH$ | 99.5° C. |
| 2-Methylpropanol | $(CH_3)_2CHCH_2OH$ | 108° C. |
| 1-Pentanol | $CH_3(CH_2)_4OH$ | 138° C. |
| 2-Pentanol | $CH_3CH_2CH_2CH(CH_3)OH$ | 119° C. |
| 3-Pentanol | $(CH_3CH_2)_2CHOH$ | 116° C. |
| 3-Methyl-1-butanol | $(CH_3)_2CHCH_2CH_2OH$ | 131° C. |
| 3-Methyl-2-butanol | $(CH_3)_2CHCH(CH_3)OH$ | 129° C. |
| 1-Hexanol | $CH_3(CH_2)_5OH$ | 156° C. |
| 1,2-Ethanediol (Ethylene glycol) | $HOCH_2CH_2OH$ | 197° C. |
| 1,2-Propanediol | $CH_3CH(OH)CH_2OH$ | 187° C. |

Table II-continued

Alcohols and Phenols

| Name | Structure | bp |
|---|---|---|
| (Propylene glycol) | | |
| 1,3-Propanediol | HOCH$_2$CH$_2$CH$_2$OH | 215° C. |
| 1,4-Butanediol | HO(CH$_2$)$_4$OH | 230° C. |
| 2-Methoxyethanol | CH$_3$OCH$_2$CH$_2$OH | 124° C. |
| 2-Ethoxyethanol | C$_2$H$_5$OCH$_2$CH$_2$OH | 135° C. |
| 2-(1-Propoxy)ethanol | CH$_3$CH$_2$CH$_2$OCH$_2$CH$_2$OH | 150° C. |
| 2-(1-Methylethoxy)ethanol | (CH$_3$)$_2$CHOCH$_2$CH$_2$OH | 144° C. |
| 2-(1-Butoxy)ethanol | CH$_3$(CH$_2$)$_3$OCH$_2$CH$_2$OH | 171° C. |
| 2-(2-methylpropoxy)-ethanol | (CH$_3$)$_2$CHCH$_2$OCH$_2$CH$_2$OH | 159° C. |
| 3-Methoxy-1-propanol | CH$_3$O(CH$_2$)$_3$OH | 153° C. |
| 3-Ethoxy-1-propanol | C$_2$H$_5$O(CH$_2$)$_3$OH | 162° C. |
| 3-(1-Propoxy)-1-propanol | CH$_3$CH$_2$CH$_2$O(CH$_2$)$_3$OH | 170° C. |
| 1-(1-Butoxy)-2-propanol | CH$_2$CH$_2$CH$_2$CH$_2$OCH$_2$CH(OH)CH$_3$ | 171° C. |
| 4-Ethoxy-1-butanol | C$_2$H$_5$O(CH$_2$)$_4$OH | 180° C. |
| 1-(2-Methoxypropoxy)-2-butanol | (CH$_3$)$_2$CHCH$_2$OCH(OH)CH$_2$CH$_3$ | 72° C. (14 mm) |
| 2-Acetoxyethanol | CH$_3$CO$_2$CH$_2$CH$_2$OH | 187° C. |
| Phenols | | |
| Phenol | C$_6$H$_5$OH | 182° C. |
| 2-Methylphenol (2-Cresol) | 2-CH$_3$C$_6$H$_4$OH | 191° C. |
| 3-Methylphenol (3-Cresol) | 3-CH$_3$C$_6$H$_4$OH | 202° C. |
| 4-Methylphenol (4-Cresol) | 4-CH$_3$C$_6$H$_4$OH | 202.5° C. |
| 2-Ethylphenol | 2-C$_2$H$_5$C$_6$H$_4$OH | 207° C. |
| 3-Ethylphenol | 3-C$_2$H$_5$C$_6$H$_4$OH | 214° C. |
| 4-Ethylphenol | 4-C$_2$H$_5$C$_6$H$_4$OH | 219° C. |
| 2-(1-Propyl)phenol | 2-CH$_3$CH$_2$CH$_2$C$_6$H$_4$OH | 220° C. |
| 3-(1-Propyl)phenol | 3-CH$_3$CH$_2$CH$_2$C$_6$H$_4$OH | 229° C. |
| 4-(1-Propyl)phenol | 4-CH$_3$CH$_2$CH$_2$C$_6$H$_4$OH | 230° C. |
| 2-(2-Propyl)phenol | 2-(CH$_3$)$_2$CHC$_6$H$_4$OH | 212° C. |
| 3-(2-Propyl)phenol | 3-(CH$_3$)$_2$CHC$_6$H$_4$OH | 228° C. |
| 4-(2-Propyl)phenol | 4-(CH$_3$)$_2$CHC$_6$H$_4$OH | 228° C. |
| 2-(1-Butyl)phenol | 2-CH$_3$(CH$_2$)$_3$C$_6$H$_4$OH | 234° C. |
| 3-(1-Butyl)phenol | 3-CH$_3$(CH$_2$)$_3$C$_6$H$_4$OH | 247° C. |
| 4-(1-Butyl)phenol | 4-CH$_3$(CH$_2$)$_3$C$_6$H$_4$OH | 248° C. |
| 2-(2-Butyl)phenol | 2-CH$_3$CH$_2$CH(CH$_3$)C$_6$H$_4$OH | 227° C. |
| 4-(2-Butyl)phenol | 4-CH$_3$CH$_2$CH(CH$_3$)C$_6$H$_4$OH | 240° C. |
| 3,5-Dimethylphenol | 3,5-(CH$_3$)$_2$C$_6$H$_3$OH | 222° C. |
| 5-Methyl-2-(2-propyl)-phenol (Thymol) | 2-(CH$_3$)$_2$CH-5-CH$_3$C$_6$H$_3$OH | 232° C. |
| 2-Methyl-5-(2-propyl)-phenol (Carvacrol) | 2-CH$_3$-5-(CH$_3$)$_2$CHC$_6$H$_3$OH | 237° C. |
| 3,5-Diethylphenol | 3,5-(C$_2$H$_5$)$_2$C$_6$H$_3$OH | 250° C. |
| 2,4-Diethylphenol | 2,4-(C$_2$H$_5$)$_2$C$_6$H$_3$OH | 228° C. |
| 2-Fluorophenol | 2-FC$_6$H$_4$OH | 171° C. |
| 3-Fluorophenol | 3-FC$_6$H$_4$OH | 178° C. |
| 4-Fluorophenol | 4-FC$_6$H$_4$OH | 185° C. |
| 2-Chlorophenol | 2-ClC$_6$H$_4$OH | 175° C. |
| 3-Chlorophenol | 3-ClC$_6$H$_4$OH | 214° C. |
| 4-Chlorophenol | 4-ClC$_6$H$_4$OH | 217° C. |
| 2,4-Dichlorophenol | 2,4-Cl$_2$C$_6$H$_3$OH | 218° C. |
| 2-Bromophenol | 2-BrC$_6$H$_4$OH | 195° C. |
| 3-Bromophenol | 3-BrC$_6$H$_4$OH | 236° C. |
| 4-Bromophenol | 4-BrC$_6$H$_4$OH | 235° C. (238 mm) |
| 3-Chloro-2-methylphenol | 3-Cl-2-CH$_3$C$_6$H$_3$OH | 225° C. |
| 4-Chloro-2-methylphenol | 4-Cl-2-CH$_3$C$_6$H$_3$OH | 222° C. |
| 5-Chloro-2-methylphenol | 5-Cl-2-CH$_3$C$_6$H$_3$OH | 210° C. |
| 6-Chloro-2-methylphenol | 6-Cl-2-CH$_3$C$_6$H$_3$OH | 185° C. |
| 2-Chloro-3-methylphenol | 2-Cl-3-CH$_3$C$_6$H$_3$OH | 198° C. |
| 4-Chloro-3-methylphenol | 4-Cl-3-CH$_3$C$_6$H$_3$OH | 235° C. |
| 6-Cloro-3-methylphenol | 6-Cl-3-CH$_3$C$_6$H$_3$OH | 196° C. |
| 2-Chloro-4-methylphenol | 2-Cl-4-CH$_3$C$_6$H$_3$OH | 195° C. |
| 3-Chloro-4-methylphenol | 3-Cl-4-CH$_3$C$_6$H$_3$OH | 228° C. |
| 2-Bromo-4-methylphenol | 2-Br-4-CH$_3$C$_6$H$_3$OH | 213° C. |
| 2-Methoxyphenol | 2-CH$_3$OC$_6$H$_4$OH | 205° C. |
| 3-Methoxyphenyl | 3-CH$_3$OC$_6$H$_4$OH | 244° C. |
| 4-Methoxyphenol | 4-CH$_3$OC$_6$H$_4$OH | 243° C. |
| Methyl 2-hydroxybenzoate (methyl salicylate) | 2-CH$_3$O$_2$CC$_6$H$_4$OH | 220° C. |
| Methyl 3-hydroxybenzoate | 3-CH$_3$O$_2$CC$_6$H$_4$OH | 280° C. |
| Methyl 4-hydroxybenzoate | 4-CH$_3$O$_2$CC$_6$H$_4$OH | 270° C. |

Catalysts which are useful in the process of the invention generally belong to the Lewis acid class of compounds. The absence of any catalyst, or the use of solid materials such as pure silica (SiO$_2$) or glass beads, which do not belong to this class, is ineffective. Suitable solid phase catalysts include titanium dioxide ($TiO_2$), alumina ($Al_2O_3$) zirconium dioxide ($ZrO_2$), molybdena ($MoO_3$), cerium (IV) oxide ($CeO_2$), mixtures of silica and alumina comprising from 10 to 100% alumina and from 90 to 0% silica, mixtures of titanium dioxide and alumina comprising from 0 to 100% titanium dioxide and 100 to 0% alumina, and supported catalysts comprising from 5 to 25% of vanadium pentoxide ($V_2O_5$), nickel oxide (NiO) or tungsten (VI) oxide ($WO_3$) on alumina or alumina-silica mixture as defined above, and mixtures of copper (II) oxide (CuO) and chromium (III) oxide ($Cr_2O_3$).

Specific catalysts included within the scope of the invention are shown in Table III.

Prior to reaction, the catalysts may be heat-treated at elevated temperatures, up to 450° C., for periods of up to one hour, with or without a current of an inert gas such as nitrogen, helium or argon passing through the hot catalyst. This heat treatment activates the catalyst by removal of water and other volatile impurities, often improves the resistance of the catalyst to attrition, and is particularly useful in regenerating spent catalysts. In the latter case, oxygen is passed through the hot catalyst after use.

The catalyst can be used in the process of this invention as a powder in the form of fluidized particles, as a fixed bed, as a counter-current or over-current bed, or as particles or pellets. Particles are produced by crushing the bulk catalyst and selecting the material which passes through a coarse standard screen such as 8-12 mesh. Pellets are produced by compacting powdered material under pressure, and may be from 0.5 to 5.0 mm in linear dimensions.

Table III

| Name | Catalysts Composition | Surface Area/gram |
|---|---|---|
| Titanium Dioxide, Fisher Scientific Co. | $TiO_2$ | |
| Harshaw Al 0104 | 99+%$Al_2O_3$ | 80-100 $m^2/g$ |
| Norton LA 6273 | 100%$Al_2O_3$ | 220 $m^2/g$ |
| Harshaw Al 1602 | 91%$Al_2O_3$ 6%$SiO_2$ | 225 $m^2/g$ |
| Linde Molecular Sieve 33-411 $NH_4Y$ Zeolite | 34%$Al_2O_3$ 66%$SiO_2$ | 593 $m^2/g$ |
| Houdry S-90 | 12.4%$Al_2O_3$ 87.3%$SiO_2$ | 430 $m^2/g$ |
| Houdry S-36 | 12.4%$Al_2O_3$ 87.3%$SiO_2$ | 190 $m^2/g$ |
| Harshaw T 0102T | 14%$Al_2O_3$ 86%$TiO_2$ | |
| Zirconium Dioxide, Fisher Scientific Co. | $ZrO_2$ | |
| Harshaw Mo 1201T Molybdena | $MoO_3$ | |
| Cerium (IV) oxide | $CeO_2$ | |
| Harshaw V0701 | 10%$V_2O_5$ on $SiO_2/Al_2O_3$ | 139 $m^2/g$ |
| Harshaw Ni0707 | 14%NiO on $Al_2O_3$ | 140 $m^2/g$ |
| Harshaw Cu0203 | 80%CuO 17%$Cr_2O_3$ | |
| Harshaw W0801 | 10%$WO_3$ on $Al_2O_3$ | 145 $m^2/g$ |

The process of the invention is a heterogeneous one in which vapor-phase reactants pass over a solid catalyst. Therefore, the reaction to form products occurs by adsorption of the reactants onto the surface, followed by desorption of the products of the reaction into the vapor stream. Adsorption of the reactants, reaction to form product molecules, and desorption of the product control the rate of the overall reaction. These controlling factors are a function of the chemical nature of the surface and of the surface area of the catalyst particles. For a given catalyst and reactants at a specified temperature, pressure and flow rate or contact time, the rate and yield of the reaction will be affected as the surface area per unit weight (specific surface) of the particles is increased. Specific surface areas are usually expressed in square meters per gram ($m^2/g$). Catalysts with surface areas in the range of 10–1000 $m^2/g$ are useful in the process of the invention and those in the range of 80 to 600 $m^2/g$ are especially preferred because of their availability.

The reaction is carried out continuously or semi-continuously in the vapor phase at temperatures of from 100° to 400° C., pressures of from 0.01 to 100 atmospheres, and contact times of from 0.1 to 20 sec, in which there is at least a 1:1 molar ratio of alcohol or phenol to amide in the reactant feed.

At temperatures below 100° C., substantially no reaction occurs. At temperatures above 400° C., side reactions such as dehydration of the alcohol or amide component, polymerization of unsaturated materials, and thermal degradation of product esters occur. The preferred temperature range is 200°–275° C. and a temperature of about 250° C. is especially preferred for ease of operation.

Reaction at pressures below 0.01 atm and above 100 atm are limited only by the constraints of equipment design. Pressures below 1 atm are especially useful when the reactants and/or products are not especially volatile or thermally stable, and when it is desired to decrease the contact time in the reaction zone. Pressures above 1 atm may be useful in some applications of the process, but will not beneficially influence the equilibrium position of the reaction because no volume change occurs when reactants are converted to products entirely in the vapor phase in the reaction zone (Le Chatelier's principle, S. Glasstone, "Textbook of Physical Chemistry", 2nd edition, Macmillan, London, 1948, p. 831). The preferred pressure for the reaction is from 0.2 to 5 atm, especially about 1 atm.

The combined operations of rate of addition, control of reactor temperature and pressure, and rate of removal of product from the reactor influence the residence time of product in the reactor. It may be desirable to shorten the residence time for a given product, because of the side effects mentioned above, by controlling the contact time. Contact time is the average time that the reactant-product mixture is in contact with the catalyst. Broadly, contact times of from 0.1 to 20 sec are useful in the process of the invention, with preferred contact times in the range of 2 to 10 sec.

The stoichiometry of the process of this invention requires amounts of carboxylic acid amide and at least equimolar amounts of alcohol or phenol to be present as reactants. The ratio of amide:alcohol actually used will depend upon what is needed to give satisfactory operation for a particular reaction. It is not detrimental to use an excess of alcohol or phenol, and may be beneficial. The Law of Mass Action (see S. Glasstone, "Textbook of Physical Chemistry", 2nd edition, Macmillan, London, 1948, page 816) indicates that excess alcohol will enhance ester formation in such a reversible reaction system. Unreacted alcohol or phenol may be recovered and recycled. However, if the amount of alcohol or phenol chosen is in large excess, the process becomes uneconomical as a result of the higher investment required in larger equipment, larger inventory of solvent, larger energy expenditures in heating the reactants, and means to separate unreacted solvent from the ester product. Broadly, carboxylic acid amide:alcohol or phenol ratios within the range of 1:1 to 1:20 are useful in the process of the invention, with ratios within the range of 1:4 to 1:8 being preferred. Alternatively, a suitable inert aliphatic or alicyclic ether such as 1,4-dioxan, 1,2-dimethoxyethane (glyme), 1-methoxy-2-(2-methoxyethoxy)ethane (diglyme), or tetrahydrofuran may be incorporated into one or more of the feed materials to promote solubility of solid reactants for ease of introduction into th reaction tube. Large amounts of such solvents are subject to the uneconomical restrictions given above.

The process can be carried out in any one of a number of ways known to those skilled in the art. The reactant feed or feeds are vaporized before or at the moment when they enter the hot catalyst reaction zone. This can be achieved by allowing a controlled stream of liquid reactants (or their mixtures with one another or with a solvent) to pass through a heated zone prior to contacting the catalyst, the temperature of this heated space being sufficient to essentially vaporize the reactant mixture. Another method of operation is to vaporize the reaction mixture or the reactants in a heated evaporator connected, in turn, to a liquid trap which returns condensate to the evaporator, and to the hot catalyst zone where reaction occurs. A third variation is to atomize or vaporize the heated reactants by means of a stream of inert carrier gas such as nitrogen, helium or argon which passes over or through the catalyst zone.

The product ester and unreacted starting materials can be collected by cooling the exit vapors from the hot catalyst zone. Ammonia or other volatile amines arising from the nitrogenous portion of the amide molecule may be present in the uncondensed portion of the exit vapors. Such ammonia or amines are readily separated from an inert carrier gas by known procedures. The product ester is identified in the condensate by conventional analytical means such as vapor phase chromatography using a pure sample of this product as an internal standard, if necessary. Such vapor phase chromatographic analysis optionally includes temperature programming for the separation of products of widely differing volatility and retention characteristics, and a coupled mass spectrometer for confirmatory mass measurement of the reaction product. The product ester can be isolated by the conventional techniques of distillation or preparative vapor phase chromatography, and can be identified by standard analytical and spectroscopic techniques. The actual conditions of separation and identification depend upon the nature of the materials, and are readily determined by one skilled in the art of organic synthesis and analysis.

The process of this invention may be carried out in a Pyrex® glass pyrolysis tube of suitable dimensions mounted vertically and packed with one or more of the catalysts described above. Inlet tubes are provided for introducing an inert carrier gas or oxygen for regeneration of spent catalyst, and for introducing reactants. The reactants are delivered at a predetermined rate by means of a motor-driven syringe. The reaction zone (pyrolysis zone) containing the catalyst is heated electrically, and the exterior and interior temperatures are monitored by thermocouples. The effluent vapors from the reaction zone are collected in a cooled trap. An inert carrier gas may be used to assist the transfer of reactants into the reaction zone and the removal of products from it, and oxygen may be used to regenerate the catalyst after each run. As a variation of this procedure, the reactants may be vaporized using a heated Pyrex® glass evaporator equipped with a liquid recycling trap.

An especially preferred process of the invention is the conversion of methacrylamide (2-methyl-2-propenamide) to methyl methacrylate (methyl 2-methyl-2-propenoate) and ammonia using methanol as shown in the equation:

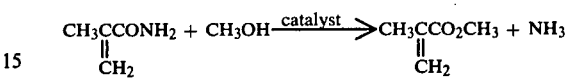

The preferred catalysts for this process are alumina-silica mixtures containing about 90% alumina and 10% silica, and zirconium dioxide. Preferred temperatures are in the range of 200°–275° C., the most preferred being about 250° C., and preferred pressures are in the range of 0.2 to 5 atm, the most preferred being about 1 atm. The methacrylamide:methanol feed ratio is in the range of 1:4 to 1:20, preferably from 1:4 to 1:8.

The effects of feed rate upon product distribution were determined for the above process in an experimental reactor which contained 20 ml (19 g) of 90% alumina and 10% silica catalyst at 250° C., in which 10 ml of a methanol solution containing 0.0354 mole of methacrylamide were pyrolyzed, with the following results:

| | Product Distribution | | |
|---|---|---|---|
| Feed Rate | Methyl Methacrylate | Methacrylo-nitrile | Total Yield |
| 1.39 ml/min | 1 | 1.24 | 0.0193 mole |
| 1.88 ml/min | 0 | 1 | 0.0215 mole |

The above data indicate that feed rate must be sufficiently low in a given system to insure adequate contact times of reactants in the presence of the catalyst to provide conversion to the desired products, in this case methyl methacrylate and recoverable ammonia.

For experimental purposes, the use of 20 ml of catalyst and 10 ml of reactant solution with a 1:4 molar ratio of amide to alcohol generally at a feed rate of 0.4 ml/min was chosen as a suitable set of conditions.

EXAMPLES

The following examples further illustrate the process of this invention. The examples given are for illustrative purposes only and the invention is not intended to be limited or restricted in any way by these specific embodiments.

EXAMPLE 1

Conversion of Methacrylamide to Methyl Methacrylate Using Titanium Dioxide Catalyst at 400° C.

The following reaction was carried out:

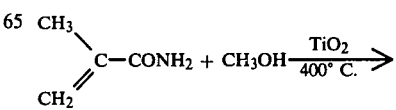

-continued

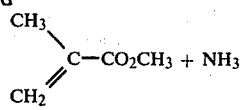

The apparatus used for this experiment included a pyrolysis tube of 30 mm diameter Pyrex ® glass mounted vertically in a furnace whose temperature was controlled by a thermocouple located outside the wall of the tube. The tube had an axial thermocouple well to measure internal temperature and an inlet for nitrogen and for the mixture of amide and alcohol used as the reaction solution. The overall length of the pyrolysis tube was 15″ (38.1 cm) and the heated portion was 12″ (30.5 cm) long. The bottom 9″ (22.8 cm) of the heated portion of the tube were packed with pelleted titanium dioxide and the top 3″ (7.6 cm) of the heated portion were void. The reaction solution consisted of 7.5 g of methacrylamide dissolved in 18 ml of methanol. The pyrolysis tube and titanium dioxide were heated to 400° C., and 10 ml of the reaction solution were delivered to the heated space above the catalyst bed at the rate of 0.040 ml per min from a hypodermic syringe driven by a Sage ® pump (manufactured by Sage Instruments, Division of Orion Research, Inc., Cambridge, Mass.).

The product was collected at the bottom of a pyrolysis tube in a flask which was cooled using a mixture of solid carbon dioxide and acetone. The product weighed 5.76 g and consisted of about ⅛ of a yellow liquid and ⅞ of a denser, colorless liquid. These were separated and each was analyzed by vapor phase chromatography (hereinafter vpc) using an 8′×⅛″ column containing 10% Triton ® 305 (an alkyl/aryl polyether manufactured by Rohm & Haas Co.) absorbed on 60/80 mesh Chromosorb ® W NAW (a diatomaceous earth fluxed above 900° C. with 2% sodium carbonate). The temperature of the chromatographic column was controlled so that during the first 3 min of the analysis it was 50° C., following which the temperature was increased at the rate of 10° C. per min until it reached 200° C., where it remained for the rest of the analysis. The flow rate of carrier gas (helium) was 45 ml/min.

Analysis of the less dense liquid showed that over 30 components were present, the principal component being methyl methacrylate (identified by spiking) in an amount of about 20±10%. The denser liquid had 9 components, of which methyl methacrylate was a minor one, in an amount of about 3±2%.

In a similar experiment in which the pyrolysis tube was packed with glass beads, no methyl methacrylate was produced. The lowest temperature at which formation of methyl methacrylate could be detected in the absence of catalyst was 700° C. This experiment indicates that the process of this invention may be carried out in the absence of catalyst at sufficiently high temperatures. However, such a process is uneconomical and energy-consuming, and the catalyzed process is preferred.

EXAMPLE 2

Conversion of Methacrylamide to Methyl Methacrylate Using Titanium Dioxide Catalyst at 300° C.

The procedure of Example 1 was followed except that the temperature of the titanium dioxide catalyst was maintained at 300° C. The product weighed 7.63 g and was a clear, single-phase yellow liquid. It was analyzed by vpc as described in Example 1 and found to contain methyl methacrylate and methacrylonitrile as the principal components in amounts of about 15±5% and 20±10%, respectively. This was confirmed by mass spectroscopy.

EXAMPLE 3

Conversion of Methacrylamide to Methyl Methacrylate Using Titanium Dioxide Catalyst at 250° C.

The procedure of Example 1 was followed except that the temperature of the titanium dioxide catalyst was maintained at 250° C. The product weighed 7.61 g and was a clear yellow liquid. The vpc analysis indicated that the principal components of the product were methyl methacrylate and methacrylonitrile. Comparison of the areas of the vpc chromatograms of the product and a sample of the product to which a measured amount of methyl methacrylate had been added showed that about 37% of the methacrylamide had been converted to methyl methacrylate.

EXAMPLE 4

Conversion of Methacrylamide to Methyl Methacrylate Using Alumina Catalyst at 175° C.

The apparatus used in this experiment was the same as used in Example 1. The reactor was charged with Harshaw Al 0104, a pelleted alumina catalyst (99+% $Al_2O_3$) having a surface area of 80 to 100 $m^2$/g. The catalyst was dehydrated by heating it at 200° C. for 1 hr. Ten milliliters of reaction solution as described in Example 1 were pyrolyzed at 175° C. at a feed rate of 0.040 ml/min. The product weighed 5.66 g and was a clear, colorless liquid. Vpc analysis following the procedure of Example 3 indicated that the methacrylamide had completely reacted and that 20% had been converted to methyl methacrylate.

EXAMPLE 5

Conversion of Acetamide to Methyl Acetate Using Titanium Dioxide Catalyst at 300° C.

The following reaction was carried out:

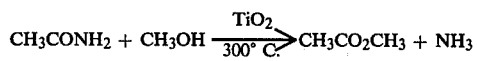

The apparatus and titanium dioxide catalyst used in this experiment were the same as those used in Example 1. The catalyst was calcined at 400° C. for 1 hr. Ten milliliters of a solution of 5 g of acetamide and 15 ml of methanol were pyrolyzed at a rate of 0.143 ml per min at 300° C. The product weighed 8.43 g and was a pale yellow liquid. A vpc analysis indicated that most of the acetamide had reacted and that the principal components of the product were methyl acetate and acetonitrile in amounts of 50±20% and 40±15%, respectively. The identity of the components was confirmed by mass spectrometry.

EXAMPLES 6 to 14

Conversion of Methacrylamide to Methyl Methacrylate Using Various Catalysts at 250° C.

In these Examples a reaction tube similar to that of Example 1 was used except that the portion of the tube holding the catalyst had a diameter of 15 mm. The reactor was charged with 20 ml of the catalyst specified in Table IV, which had been conditioned by heating it in a stream of nitrogen (flow rate ~50 ml/min) as indicated in Table IV. Ten milliliters of a solution prepared according to Example 1 were pyrolyzed. After all the solution had discharged, the products were swept from the catalyst in a stream of nitrogen (flow rate ~50 ml/min) applied for 0.5 hr while the catalyst was maintained at the pyrolysis temperature. The product was analyzed following the procedure of Example 1. The results are shown in Table IV in which the following abbreviations are used: MMA=methyl methacrylate; MAN=methacrylonitrile; MAA=methacrylamide.

which insured that the reactants encountered the catalyst as gases and did not fractionally evaporate on the catalyst surface. A glass evaporator was attached at the top of the pyrolysis tube of Examples 6 to 14. The evaporator was heated electrically to 450° C. and included a trap to insure that reactants which entered as a liquid could leave only as gaseous reactants. A heater extended from the evaporator down to the pyrolysis tube to prevent condensation of the gaseous reactants.

The pyrolysis tube was charged with 20 ml (13.7 g) of Norton LA 6273, 100% alumina catalyst which was Table IV

CONVERSION OF METHACRYLAMIDE TO METHYL METHACRYLATE

| Example | Catalyst (g) | Reaction Conditions Pre-Treatment | Feed Rate (ml/min) | Temp | Products (Moles) MMA | MAN | MAA | MMA Conv % | Yield % | Conversion rate (g/g cat-hr) |
|---|---|---|---|---|---|---|---|---|---|---|
| 6 | Zirconium dioxide (ZrO$_2$)(Fisher Sci. Co.) | 250° C.(1 hr) | 0.040 | 250° C. | (a) | (a) | (a) | (a) | (a) | (a) |
| 7[b] | 2Molecular Sieve 33-411 NH$_4$-Y Zeolite Surface area 593 m$^2$/g (66% SiO$_2$, 34% Al$_2$O$_3$) | 250° C.(0.5 hr) | 0.040 | 250° C. | 0.0100 | (a) | (a) | 29 | (a) | (a) |
| 8[b] | Harshaw T 0102T (86% TiO$_2$, 14% Al$_2$O$_3$) | 250° C.(0.5 hr) | 0.040 | 250° C. | 0.0130 | 0.0070 | trace | 37 | 45 | about 0.016 |
| 9[c] | Titanium dioxide (TiO$_2$)(Fisher Sci. Co.) | 250° C.(0.5 hr) | 0.040 | 250° C. | 0.0150 | 0.0120 | trace | 45 | 65 | about 0.019 |
| 10[c] | Norton LA 6273 (13.5) (100% Al$_2$O$_3$) surface area 220 m$^2$/g | 450° C.(2 hr) | 0.40 | 250° C. | 0.0125 | 0.0012 | 0.0073 | 36 | 47 | 0.22 |
| 11[c,d] | Harshaw Al 1602 (16.4) (91% Al$_2$O$_3$, 6% SiO$_2$) surface area 225 m$^2$/g | 450° C.(1 hr) | 0.39 | 250° C. | 0.0146 | 0.0035 | 0.0048 | 42 | 54 | 0.21 |
| 12[c,e] | Houdry S-90 (10.2) (12.4 % Al$_2$O$_3$, 87.3% SiO$_2$) Surface area 430 m$^2$/g | 450° C.(1 hr) | 0.39 | 250° C. | 0.0084 | 0.0005 | 0.0130 | 24 | 38 | 0.19 |
| 13[c,e] | Houdry S-36 (11.3) (12.4% Al$_2$O$_3$, 87.3% SiO$_2$) Surface area 190 m$^2$/g | 450° C.(1 hr) | 0.39 | 250° C. | 0.0050 | trace | 0.0164 | 14 | 26 | 0.10 |
| 14[c,e] | Harshaw Mo 1201T (18.0) Molybdena (MoO$_x$) | 300° C.(0.5 hr) | 0.39 | 250° C. | 0.0089 | 0.0061 0.0071 | 25 | 41 | 0.12 | |

[a]Insufficient data to complete these calculations; qualitatively resembled Example 9.
[b]Added 0.0067 g of hydroquinone to stabilize amide
[c]Added 0.0067 g of phenothiazine to stabilize amide
[d]Top of reactor had a 0.5 in (1.27 cm) layer of silicon carbide as an inert reactant vaporizer
[e]Top of reactor contained a 0.5 in (1.27 cm) layer of copper shot as a polymerization inhibiting reactant vaporizer

EXAMPLE 15

Conversion of Acetamide to Methyl Acetate Using Zirconium Dioxide Catalyst at 250° C.

The apparatus of Examples 6 to 14 was used in this experiment. The reactor was charged with 20 ml of zirconium dioxide (ZrO$_2$) which had been compressed into granules to pass a screen between 8 and 12 mesh. This catalyst was calcined under nitrogen at 250° C. for 0.5 hr. A reaction solution was prepared from 3.1 g of acetamide and methanol to make 15 ml of solution. Ten milliliters of this solution were pyrolyzed at 250° C. at the rate of 0.040 ml per min. After the reaction, nitrogen was passed over the catalyst at 250° C. for 0.5 hr at a flow rate of 50 ml per min to assist recovery of the product which was 8.18 g of clear colorless liquid. Vpc analysis showed that the acetamide was completely consumed, and that 67% of it was converted to methyl acetate and 33% to acetonitrile.

EXAMPLE 16

Conversion of Methacrylamide to Methyl Methacrylate Using a Pre-evaporator and an Alumina Catalyst at 250° C.

In this example the apparatus used in the foregoing examples was modified by incorporating an evaporator calcined at 300° C. for 0.5 hr in a slow current of nitrogen. The reaction mixture was prepared from 4.5 g of methacrylamide, 0.1 g of phenothiazine and methanol to make 15 ml of solution. Ten milliliters of this solution were pyrolyzed at 250° C. at a rate of 0.39 ml per min. After the reaction the products were recovered by passing nitrogen (flow rate ~50 ml/min) over the catalyst at 250° C. for 0.5 hr. The product was 7.57 g of very pale yellow clear liquid.

A vpc analysis showed that 81% of the methacrylamide had reacted, of which 32% was converted to methyl methacrylate.

EXAMPLE 17

Conversion of Methacrylamide to Methyl Methacrylate Using Cerium (IV) Oxide Catalyst at 250° C.

Cerium (IV) oxide (CeO$_2$) catalyst was prepared by heating cerium oxalate (Ce$_2$(C$_2$O$_4$)$_3$.9H$_2$O), first at 250° C. for 4 hr, then at 550° C. for a further 4 hr. This powdered oxide was pressed into small agglomerates (8 to 12 mesh) and 20 ml (33.6 g) of these were charged into a reactor similar to that used in Example 16. The catalyst was calcined at 300° C. for 1 hr under nitrogen, and then 10 ml of a solution of methacrylamide in methanol, prepared as in Example 16, were pyrolyzed in the reactor at 250° C. at a rate of 0.39 ml per min.

The product was 8.0 g of pale yellow liquid. A vpc analysis showed that 93% of the methacrylamide had reacted, 29% of which had been converted to methyl methacrylate.

EXAMPLE 18

Conversion of Benzamide to Methyl Benzoate Using An Alumina Catalyst at 250° C.

The following reaction was carried out:

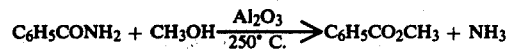

The apparatus of Example 16 was used in this Example. The reactor was charged with 20 ml (17.0 g) of Harshaw Al 1602 catalyst, (91% Al₂O₃, 6% SiO₂, surface area 225 m²/g) and this was calcined at 300° C. for 1 hr under nitrogen (flow rate ∼ 50 ml/min). A reaction solution was prepared from 4.5 g of benzamide and 20 ml of methanol (combined vol. 23.3 ml). Ten milliliters of this solution were pyrolyzed at the rate of 0.39 ml/min at 250° C.

The product was a clear, colorless liquid weighing 7.40 g. It was analyzed by vpc using the technique of Example 1. The benzamide was completely consumed and 41% of it had been converted to methyl benzoate.

EXAMPLE 19

Conversion of Acetamide to Ethyl Acetate Using An Alumina Catalyst at 250° C.

The following reaction was carried out:

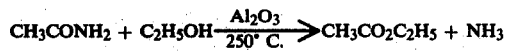

The apparatus of Example 16 was used in this Example. The reactor was charged with Harshaw Al 1602 (91% Al₂O₃, 6% SiO₂) catalyst and preheated as in Example 18. A reaction solution was prepared from 3.0 g of acetamide and 12.9 ml of ethanol (15.0 ml total volume). Ten milliliters of this solution were pyrolyzed at the rate of 0.39 ml/min at 250° C.

The product was a clear, colorless liquid weighing 7.83 g. It was analyzed by vpc using the technique of Example 1. All the acetamide had reacted and 49% of it had been converted to ethyl acetate.

EXAMPLE 20

Conversion of Acetamide to Isopropyl Acetate Using Titanium Dioxide Catalyst at 250° C.

The following reaction was carried out:

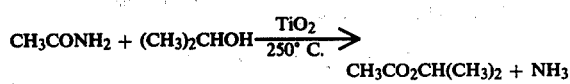

The apparatus of Example 16 was used. The pyrolysis tube was charged with 20 ml (21.0 g) of compacted titanium dioxide (TiO₂) and this was calcined at 300° C. for 1 hr under nitrogen. A solution of 3.0 g of acetamide in 18 ml of isopropyl alcohol was prepared. Ten milliliters of this solution were pyrolyzed at 250° C. at a rate of 0.39 ml/min. The product was a clear colorless liquid weighing 7.99 g.

A vpc analysis using a 6'×⅛" column of 20% X E60 on 80/100 mesh Gas Chrom R under the conditions described in Example 1 indicated that 28% of the acetamide had been converted to isopropyl acetate.

EXAMPLE 21

Conversion of Benzamide to Isopropyl Benzoate Using Titanium Dioxide Catalyst at 250° C.

The following reaction was carried out:

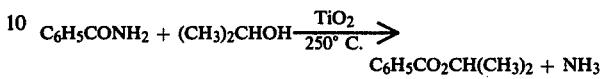

The apparatus of Example 16 was used. The pyrolysis tube was charged with titanium dioxide (TiO₂) catalyst as in Example 20. The reaction solution was prepared from 1.0 g of benzamide and 20 ml of isopropyl alcohol (combined volume 20.6 ml). Ten milliliters of this solution were pyrolyzed at 250° C. at a rate of 0.39 ml/min.

The product was a clear colorless liquid weighing 7.68 g. It was analyzed by vpc as in Example 1. All of the benzamide had reacted and 45% of it had been converted to isopropyl benzoate.

EXAMPLE 22

Conversion of Acrylamide to Methyl Acrylate Using An Alumina-Silica Catalyst at 250° C.

The following reaction was carried out:

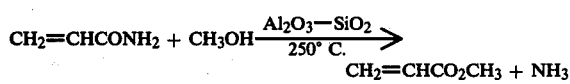

Using the apparatus of Example 16, the catalyst tube was charged with 20 ml (15.6 g) of Harshaw Al 1602 (91% Al₂O₃+6% SiO₂) catalyst. The catalyst was conditioned by heating to 300° C. for 0.5 to 1 hr in nitrogen. A reaction solution was prepared from 4.5 g of acrylamide, 0.1 g of phenothiazine and 11.1 ml of methanol (total volume 15 ml). Ten milliliters of this solution were pyrolyzed at 250° C. at a rate of 0.39 ml per min.

The products obtained were 6.61 g of clear colorless liquid and a small amount of white solid on top of the catalyst bed.

The liquid component was analyzed by vpc on a 10'×⅛" column containing 10% Ucon LLB 550X on 100/120 mesh Gas Chrom R under the temperature conditions described in Example 1. This analysis indicated that about 1% of the acrylamide had been converted to methyl acrylate. The carbon, hydrogen and nitrogen content of the white solid suggest that it is polyacrylamide.

Anal. Calcd. for $(C_3H_5NO)_n$: C, 50.70%; H, 7.04%; N, 19.72%. Found: C, 51.54%; H, 6.90%; N, 19.38%.

EXAMPLE 23

Conversion of Butanamide to Methyl Butanoate Using An Alumina Catalyst at 250° C.

The following reaction was carried out:

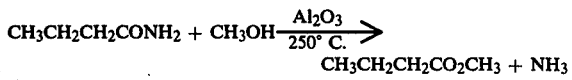

The apparatus of Example 16 was used. The pyrolysis tube was charged with 20 ml (17.5 g) of Harshaw Al 0104 pelleted 99+% alumina catalyst which was calcined at 300° C. for 1 hr under nitrogen. A reaction solution was prepared from 4.5 g of butanamide and 10.8 ml of methanol (total volume 15 ml). Ten milliliters of this solution were pyrolyzed at 250° C. at a rate of 0.39 ml per min.

The product was 7.96 g of clear colorless liquid. It was analyzed by vpc under the conditions described in Example 1. About 92% of the butanamide had reacted, 42% of which had been converted to methyl butanoate.

EXAMPLE 24

Conversion of Acetamide to 2-Acetoxyethanol Using an Alumina-Silica Catalyst at 175° C. and 48 mm Hg Pressure The following reaction was carried out:

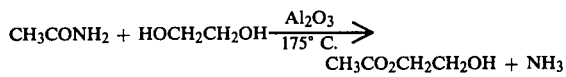
$$CH_3CONH_2 + HOCH_2CH_2OH \xrightarrow[175° C.]{Al_2O_3} CH_3CO_2CH_2CH_2OH + NH_3$$

The apparatus described in Example 16 was employed. Its vent line was attached to a vacuum pump through a manostat so that reaction could be studied at controlled reduced pressure. The reactor was charged with Harshaw Al 1602 (91% $Al_2O_3$, 6% $SiO_2$) catalyst and this was calcined as in Example 18. A reaction solution was prepared from 3.0 g of acetamide and 12.2 ml of 1,2-ethanediol (ethylene glycol) to give 15 ml of liquid. Ten milliliters of this solution were pyrolyzed at 175° C. and 48 mm Hg pressure, at an average rate of 0.097 ml per minute. Nitrogen was swept through the tube for 1 hr at 175° C. and 48 mm Hg to assist in obtaining the product.

The product was a clear colorless liquid which weighed 9.37 g. It was analyzed by vpc using a 6'×⅛" column of 20% XE-60 on 80/100 mesh Gas Chrom RA under conditions given in Example 1. The results showed that 47% of the acetamide had been converted to 2-acetoxyethanol.

EXAMPLE 25

Conversion of Acetamide to 2-Acetoxyethanol Using An Alumina-Silica Catalyst at 100° C. and 20 mm Hg Pressure This experiment establishes the low temperature limit for the process of this invention.

The procedure of Example 24 was followed except that the temperature was maintained at 100° C., the pressure was 20 mm Hg and the average flow rate was 0.11 ml per min.

The product obtained was 3.1 g of slightly turbid yellow liquid. It was analyzed by vpc using the procedure described in Example 1. About 0.3% of the acetamide had been converted to 2-acetoxyethanol.

EXAMPLE 26

Conversion of 2-Acetoxyethanol to 1,2-Ethanediyl Diacetate Using Acetamide and an Alumina-Silica Catalyst at 250° C.

The following reaction was carried out:

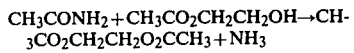
$$CH_3CONH_2 + CH_3CO_2CH_2CH_2OH \rightarrow CH_3CO_2CH_2CH_2O_2CCH_3 + NH_3$$

The apparatus of Example 16 was used. The pyrolysis tube was charged with 20 ml (15.9 g) of Harshaw Al 1602 catalyst (91% $Al_2O_3$, 6% $SiO_2$), and this was conditioned by heating at 300° C. for 1 hr in a slow (50 ml/min) stream of nitrogen. A solution was prepared from 3.0 g of acetamide and sufficient 2-acetoxyethanol to make 15 ml of solution. Ten milliliters of this solution were pyrolyzed at 250° C. and ambient pressure, at a rate of 0.39 ml per min.

The product was 9.91 g of clear yellow liquid. It was analyzed by vpc under the conditions described in Example 1. About 48% of the acetamide had been converted to 1,2-ethanediyl diacetate (ethylene glycol diacetate).

EXAMPLE 27

Conversion of Acetamide to Phenyl Acetate Using An Alumina-Silica Catalyst at 250° C.

The following reaction was carried out:

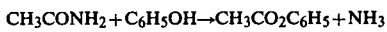
$$CH_3CONH_2 + C_6H_5OH \rightarrow CH_3CO_2C_6H_5 + NH_3$$

Using the apparatus of Example 16, the pyrolysis tube was charged with 20 ml (16 g) of Harshaw Al 1602 catalyst (91% $Al_2O_3$, 6% $SiO_2$), which was calcined for 1 hr at 300° C. under nitrogen. A reaction solution (17.2 ml) was prepared by dissolving 2 g of acetamide and 6 g of phenol in 10 ml of 1,4-dioxan. Ten milliliters of this solution were pyrolyzed at 250° C. at a rate of 0.39 ml per min.

The product was 9.29 ml of very pale yellow liquid. Analysis of the product by the procedure described in Example 1 indicated that 12% of the acetamide had been converted to phenyl acetate.

EXAMPLE 28

Conversion of N,N-Dimethylacetamide to Methyl Acetate Using An Alumina Catalyst at 250° C.

The following reaction was carried out:

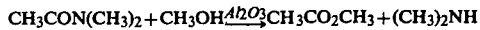
$$CH_3CON(CH_3)_2 + CH_3OH \xrightarrow{Al_2O_3} CH_3CO_2CH_3 + (CH_3)_2NH$$

The apparatus of Example 16 was employed and the pyrolysis tube was charged with 20 ml (18.2 g) of Harshaw Al 0104 catalyst (99+% $Al_2O_3$). The catalyst was calcined at 300° C. for 1 hr under a slow stream of nitrogen (about 50 ml per min). A reaction solution (15 ml) was prepared from 4.5 ml of N,N-dimethylacetamide and 10.6 ml of methanol. Ten milliliters of this solution were pyrolyzed at 250° C. at a rate of 0.39 ml per min.

The product obtained was 8.13 g of clear colorless liquid. Analysis by the procedure described in Example 1 showed that 41% of the N,N-dimethylacetamide had been converted to methyl acetate.

EXAMPLES 29–32

Conversion of Methacrylamide to Methyl Methacrylate Using Supported Metal OXide Catalysts at 250° C.

In all of these experiments the apparatus used was similar to that described in Example 16. The pyrolysis tube was charged with 20 ml of catalyst and this was calcined for 1 hr at 350° C. under nitrogen (about 50 ml per min). Ten milliliters of a solution prepared from 4.5 g of methacrylamide and 0.1 g of phenothiazine with enough methanol to make 15 ml were pyrolyzed at 250° C. at a rate of 0.39 ml per min.

The products were analyzed by vpc using the procedure described in Example 1. Results are given in Table V.

TABLE V:

| | SUPPORTED CATALYSTS | | | | | |
|---|---|---|---|---|---|---|
| | | Products (Moles) | | | MMA* | |
| Example No. | Catalyst (g) | MMA* | MAN* | MAA* | Conv. | Yield |
| 29 | Harshaw VO701 10% $V_2O_5$ on $SiO_2/Al_2O_3$ Surface area 139 m$^2$/g | 0.0096 | 0.0114 | 0.0061 | 27 | 54 |
| 30 | Harshaw Ni 0707 14% NiO on $Al_2O_3$ Surface area 140 m$^2$/g | 0.0024 | 0.0045 | 0.0119 | 7 | 13 |
| 31 | Harshaw Cu 0203 80% CuO, 17% $Cr_2O_3$ | 0.0059 | 0.0002 | 0.0062 | 17 | 20 |
| 32 | Harshaw W0801 10% $WO_3$ on $Al_2O_3$ Surface area 145 m$^2$/g | 0.0124 | 0.0073 | 0.0066 | 35 | 58 |

*MMA = Methyl Methacrylate
*MAN = Methacrylonitrile
*MAA = Methacrylamide

I claim:

1. A process for the preparation of carboxylic acid esters having the formula $RCOOR_3$ from carboxylic acid amides having the formula $RCONR_1R_2$ and hydroxyl compounds having the formula $R_3OH$, which comprises contacting at least one mole of said hydroxyl compound with each mole of said amide in the vapor phase at temperatures of from 100° C. to 400° C. and at pressures of from 0.01 to 100 atmospheres in the presence of a solid catalyst having a surface area of 10 to 1000 m$^2$/g for a contact time of 0.1 to 20 seconds, thereby forming the ester and $HNR_1R_2$, recovering the ester by condensation of the exit vapors by cooling, and separating $HNR_1R_2$ from the uncondensed portion of the exit vapors, wherein R is selected from the class consisting of H; an alkyl group having from 1 to 10 carbon atoms; an alkenyl group having from 2 to 10 carbon atoms; alkynyl having from 2 to 10 carbon atoms; phenyl; and a phenyl group substituted by a methyl, chloro or methoxy group;

$R_1$ taken separately is selected from the class consisting of H and alkyl groups having from 1 to 10 carbon atoms;

$R_2$ taken separately is selected from the class consisting of H and alkyl groups having from 1 to 10 carbon atoms;

$R_3$ is selected from the class consisting of
primary or secondary alkyl group having from 1 to 10 carbon atoms;
primary or secondary alkyl group having from 2 to 10 carbon atoms substituted by a hydroxy group, alkoxy group having from 1 to 4 carbon atoms or an acetoxy group;
phenyl; and
phenyl substituted by 1 or 2 alkyl groups having 1 to 10 carbon atoms, 1 or 2 fluorine atoms, 1 or 2 chlorine atoms, 1 or 2 bromine atoms, a methoxy group or a methoxycarbonyl group;

and the catalyst is selected from the class consisting of titanium dioxide, alumina, zirconium oxide, molybdena, cerium (IV) oxide, mixtures of from 10 to 100% alumina and 90 to 0% silica, mixtures of from 0 to 100% titanium dioxide and 100 to 0% alumina, and supported catalyst compositions comprising 5 to 25% vanadium pentoxide, nickel oxide, or tungsten oxide on alumina, alumina-silica mixtures, or copper (II) oxide and chromium (III) oxide mixtures.

2. The process of claim 1 wherein R is selected from the class consisting of H, an alkyl group having from 1 to 4 carbon atoms, an alkenyl group having from 2 to 4 carbon atoms, alkynyl having from 2 to 4 carbon atoms, a phenyl group, and a phenyl group substituted by a methyl, chloro or methoxy group.

3. The process of claim 2 wherein $R_1$ is selected from the class consisting of H and alkyl groups having from 1 to 4 carbon atoms.

4. The process of claim 3 wherein $R_2$ is selected from the class consisting of H and alkyl groups having from 1 to 4 carbon atoms.

5. The process of claim 4 wherein $R_3$ is selected from the class consisting of:
primary or secondary alkyl having from 1 to 6 carbon atoms;
primary or secondary alkyl having from 2 to 4 carbon atoms substituted by a hydroxy group, alkoxy group having from 1 to 4 carbon atoms, or an acetoxy group;
phenyl; and
phenyl substituted by 1 or 2 alkyl groups having 1 to 4 carbon atoms, 1 or 2 fluorine atoms, 1 or 2 chlorine atoms, 1 or 2 bromine atoms, a methoxy group or a methoxycarbonyl group.

6. The process of claim 5 wherein R is an alkenyl group having from 2 to 4 carbon atoms.

7. The process of claim 5 wherein:
R is

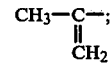

$R_1$ is H—;
$R_2$ is H—; and
$R_3$ is $CH_3$—.

8. The process of claim 5 wherein:
R is $CH_3$—;
$R_1$ is H—;
$R_2$ is H—; and
$R_3$ is $CH_3$—.

9. The process of claim 5 wherein:
R is $C_6H_5$—;
$R_1$ is H—;
$R_2$ is H—; and
$R_3$ is $CH_3$—.

10. The process of claim 5 wherein:
R is $CH_3$—;
$R_1$ is H—;
$R_2$ is H—; and
$R_3$ is $C_2H_5$—.

11. The process of claim 5 wherein:
R is $CH_3$—;
$R_1$ is H—;
$R_2$ is H—; and
$R_3$ is $(CH_3)_2CH$—.

12. The process of claim 5 wherein:
R is $C_6H_5$—;
$R_1$ is H—;
$R_2$ is H—; and
$R_3$ is $(CH_3)_2CH$—.

13. The process of claim 5 wherein:
R is $CH_2=CH$—;
$R_1$ is H—;
$R_2$ is H—; and
$R_3$ is $CH_3$—.

14. The process of claim 5 wherein:
R is $CH_3CH_2CH_2$—;
$R_1$ is H—;
$R_2$ is H—; and
$R_3$ is $CH_3$—.

15. The process of claim 5 wherein:
R is $CH_3$—;
$R_1$ is H—;
$R_2$ is H—; and
$R_3$ is $HOCH_2CH_2$—.

16. The process of claim 5 wherein:
R is $CH_3$—;
$R_1$ is H—;
$R_2$ is H—; and
$R_3$ is $CH_3CO_2CH_2CH_2$—.

17. The process of claim 5 wherein:
R is $CH_3$—;
$R_1$ is H—;
$R_2$ is H—; and
$R_3$ is $C_6H_5$—.

18. The process of claim 5 wherein:
R is $CH_3$—;
$R_1$ is $CH_3$—;
$R_2$ is $CH_3$— and
$R_3$ is $CH_3$—.

19. The process of claim 1 wherein the reaction is carried out at temperatures of from 200°–275° C., at pressures of from 0.2 to 5 atmospheres, and there is present in said reaction 4 to 20 feed moles of $R_3OH$ compound per feed mole of amide.

20. The process of claim 19 wherein the catalyst is a mixture of about 90% alumina and 10% silica.

21. The process of claim 19 wherein the catalyst is zirconium dioxide.

22. The process of claim 19 wherein:
R is

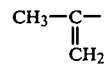

$R_1$ is H—;
$R_2$ is H—; and
$R_3$ is $CH_3$—.

23. The process of claim 19 wherein the reaction is carried out at a temperature of about 250° C., at about 1 atmosphere pressure, and there is present in said reaction 4 to 8 feed moles of $R_3OH$ compound per feed mole of amide.

24. The process of claim 23 wherein:
R is

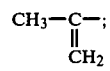

$R_1$ is H—;
$R_2$ is H—; and
$R_3$ is $CH_3$—; and the catalyst is a mixture of about 90% alumina and 10% silica, or zirconium dioxide.

25. The process of claim 1 carried out semicontinuously.

26. The process of claim 1 carried out continuously.

* * * * *